United States Patent
Finch et al.

(10) Patent No.: US 9,880,075 B2
(45) Date of Patent: Jan. 30, 2018

(54) WEAR MEASUREMENT SYSTEM USING A COMPUTER MODEL

(71) Applicant: Caterpillar Inc., Peoria, IL (US)

(72) Inventors: Nolan S. Finch, Champaign, IL (US); Yue Wang, Anhui (CN); Kook In Han, Savoy, IL (US); Timothy J. Bennett, Bloomington, IL (US); Daniel A. Smyth, Metamora, IL (US)

(73) Assignee: Caterpillar Inc., Peoria, IL (US)

( * ) Notice: Subject to any disclaimer, the term of this patent is extended or adjusted under 35 U.S.C. 154(b) by 50 days.

(21) Appl. No.: 15/041,523

(22) Filed: Feb. 11, 2016

(65) Prior Publication Data
US 2017/0234775 A1    Aug. 17, 2017

(51) Int. Cl.
*G06K 9/00* (2006.01)
*G01M 17/03* (2006.01)
(Continued)

(52) U.S. Cl.
CPC ........ *G01M 17/03* (2013.01); *G01N 21/8851* (2013.01); *G06F 17/50* (2013.01)

(58) Field of Classification Search
CPC .......... G06T 7/0002–7/001; G06T 7/60–7/68; G06T 2207/10028;
(Continued)

(56) References Cited

U.S. PATENT DOCUMENTS 5,805,289 A * 9/1998 Corby, Jr. ............... G01B 5/14
345/419
5,848,115 A    12/1998 Little et al.
(Continued)

FOREIGN PATENT DOCUMENTS

EP    0 593 183 A2    4/1994

OTHER PUBLICATIONS

B. Horn, "Closed-form Solution of Absolute Orientation Using Unit Quaternions," J. Optical Society of America, vol. 4, No. 4, pp. 629-642, Apr. 1987 (14 pages).
(Continued)

*Primary Examiner* — Aaron W Carter
(74) *Attorney, Agent, or Firm* — Finnegan, Henderson, Farabow, Garrett & Dunner, LLP

(57) ABSTRACT

A wear measurement system for a component is disclosed. The wear measurement system may include an imaging device configured to obtain a plurality of two-dimensional images of the component. The wear measurement system may also include a controller. The controller may be configured to generate a three-dimensional point cloud representing the component based on the two-dimensional images. The controller may also be configured to overlay a computer model of the component on the three-dimensional point cloud. Further, the controller may be configured to project the computer model on the two-dimensional images. The controller may also be configured to select at least two reference points appearing in each of a subset of images selected from the two-dimensional images. The controller may be configured to determine locations of the two reference points in the three-dimensional point cloud, determine an image distance between the locations, and determine an amount of wear based on the image distance.

20 Claims, 9 Drawing Sheets

(51) Int. Cl.
*G06F 17/50* (2006.01)
*G01N 21/88* (2006.01)

(58) Field of Classification Search
CPC ............ G06T 2207/30108–2207/30164; G06T 11/60; G06K 9/4661; G06K 9/52; G06K 9/6201; G01N 21/8851; G01B 11/14
See application file for complete search history.

(56) References Cited

U.S. PATENT DOCUMENTS

| | | | |
|---|---|---|---|
| 7,006,084 B1 | 2/2006 | Buss et al. | |
| 7,327,857 B2 | 2/2008 | Lloyd, Jr. et al. | |
| 8,045,791 B2 | 10/2011 | Chang et al. | |
| 8,503,757 B2 | 8/2013 | Naruse et al. | |
| 8,756,085 B1* | 6/2014 | Plummer | G06Q 40/00 705/4 |
| 8,780,223 B2 | 7/2014 | Beauchemin | |
| 8,866,891 B2 | 10/2014 | Derrien et al. | |
| 9,317,741 B2* | 4/2016 | Guigues | G06K 9/00342 |
| 9,633,146 B2* | 4/2017 | Plummer | G06F 17/5009 |
| 2008/0118143 A1* | 5/2008 | Gordon | G01B 11/2513 382/154 |
| 2010/0278418 A1* | 11/2010 | Chang | G01B 11/24 382/152 |
| 2010/0328682 A1* | 12/2010 | Kotake | G06T 7/521 356/620 |
| 2011/0211066 A1* | 9/2011 | Fujiki | H04N 7/181 348/135 |
| 2011/0317909 A1 | 12/2011 | Jeyaraman et al. | |
| 2013/0262497 A1 | 10/2013 | Case et al. | |
| 2013/0287288 A1* | 10/2013 | Bendall | G06T 7/0004 382/154 |
| 2014/0056507 A1* | 2/2014 | Doyle | G01B 11/002 382/152 |
| 2014/0105481 A1 | 4/2014 | Hasselbusch et al. | |
| 2014/0278570 A1* | 9/2014 | Plummer | G06Q 40/00 705/4 |
| 2015/0022638 A1* | 1/2015 | Saeki | G06T 7/0004 348/46 |
| 2015/0066291 A1* | 3/2015 | Johannsen | B62D 55/32 701/34.4 |
| 2015/0149049 A1* | 5/2015 | Bewley | E02F 9/2816 701/50 |
| 2015/0178412 A1* | 6/2015 | Grau | G06F 17/50 703/1 |
| 2015/0332463 A1* | 11/2015 | Galera | G06K 9/00771 382/103 |
| 2016/0117856 A1* | 4/2016 | Chang | G06T 15/00 345/427 |
| 2016/0159011 A1* | 6/2016 | Marchione | G05B 19/4207 700/98 |
| 2016/0196643 A1* | 7/2016 | Bendall | G06T 7/602 382/108 |
| 2017/0005857 A1* | 1/2017 | Reiss | H04L 41/0609 |
| 2017/0084085 A1* | 3/2017 | Solorio | G06T 19/006 |

OTHER PUBLICATIONS

K. Han and M. Golparvar-Fard, "Appearance-based Material Classification for Monitoring of Operation-Level Construction Progress Using 4D BIM and Site Photologs," Automation in Construction, vol. 53, pp. 44-57, 2015 (14 pages).

* cited by examiner

WEAR MEASUREMENT SYSTEM USING A COMPUTER MODEL

TECHNICAL FIELD

The present disclosure relates generally to a wear measurement system, and, more particularly, to a wear measurement system using a computer model.

BACKGROUND

Earth-working machines, for example, excavators, continuous miners, and loaders, often include ground engaging work tools that engage with and/or move a variety of earthen materials. Furthermore, tracked undercarriages that facilitate movement of the machines over ground surfaces and other moving parts of these machines may engage with the ground surface or earthen materials. Repeated exposure to hard work materials or the ground surface may cause one or more components of these machines to wear.

Conventional techniques for detecting wear on the machine components include manual measurements of component dimensions, which may be compared against specified dimensions of the components. Such manual measurements are not only time consuming but also can be inaccurate. Inaccurate measurements of the component dimensions in turn may result in incorrect predictions regarding the remaining life of the component. As a result, the component may either fail too early or may not be worn enough to require replacement or repair when the machine is removed from service for maintenance. Thus, there is a need for accurate measurement of component dimensions on a machine in its work environment to allow for improved component life predictions, which may help reduce the down time associated with repair or replacement of worn out components.

U.S. Pat. No. 7,327,857 B2 to Lloyd Jr. et al. ("the '857 patent") that issued on Feb. 5, 2008 discloses a non-contact measurement method and apparatus for examining an object having complex surfaces or shape deformations. The '857 patent discloses an imaging device, such as, a full-field, non-contact, laser range sensor mounted on a translation stage that provides data in three spatial dimensions (X, Y, Z) of an object. The '857 patent refers to this three-dimensional data as a scanned image. The '857 patent further discloses that a three-dimensional reference model or reference image of the object is stored in a memory. The '857 patent discloses that the reference model is registered with the three-dimensional scanned image of the object. In addition, the '857 patent discloses a gauging module that determines one or more gauging measurements as the spacing between contours of the scanned image and the reference model.

Although the '857 patent discloses the use of imaging for measurement of deformations on a component, the disclosed device and methods may still not be optimal. In particular, the disclosed device requires the use of a specialized device mounted on a translation stage and configured to generate three-dimensional spatial measurements of the component. The use of a specialized imaging device and stage may make the disclosed apparatus cumbersome to use and expensive to maintain. Moreover, the disclosed apparatus requires the component to be taken out of service for performing the measurements. Such down time may not be practical or desirable to ensure maximum utilization of the component.

The wear measurement system of the present disclosure solves one or more of the problems set forth above and/or other problems in the art.

SUMMARY

In one aspect, the present disclosure is directed to a wear measurement system for a component. The wear measurement system may include an imaging device configured to obtain a plurality of two-dimensional images of the component. The wear measurement system may also include a controller. The controller may be configured to generate a three-dimensional point cloud representing the component based on the two-dimensional images. The controller may also be configured to overlay a computer model of the component on the three-dimensional point cloud. Further, the controller may be configured to project the computer model on the two-dimensional images. The controller may also be configured to select at least two reference points appearing in each of a subset of images selected from the two-dimensional images. The controller may be configured to determine locations of the two reference points in the three-dimensional point cloud. The controller may also be configured to determine an image distance between the locations. In addition, the controller may be configured to determine an amount of wear based on the image distance.

In another aspect, the present disclosure is directed to a method of measuring wear on a component. The method may include obtaining, using an imaging device, a plurality of two-dimensional images of the component. The method may also include generating, using a controller, a three-dimensional point cloud representing the component based on the two-dimensional images. Further, the method may include overlaying a computer model of the component on the three-dimensional point cloud. The method may also include projecting the computer model on the two-dimensional images. The method may include selecting at least two reference points appearing in each of a subset of images selected from the two-dimensional images. The method may also include determining locations of the at least two reference points in the three-dimensional point cloud. The method may include determining an image distance between the locations. In addition, the method may include determining an amount of wear based on the image distance.

DETAILED DESCRIPTION

Figure 1:
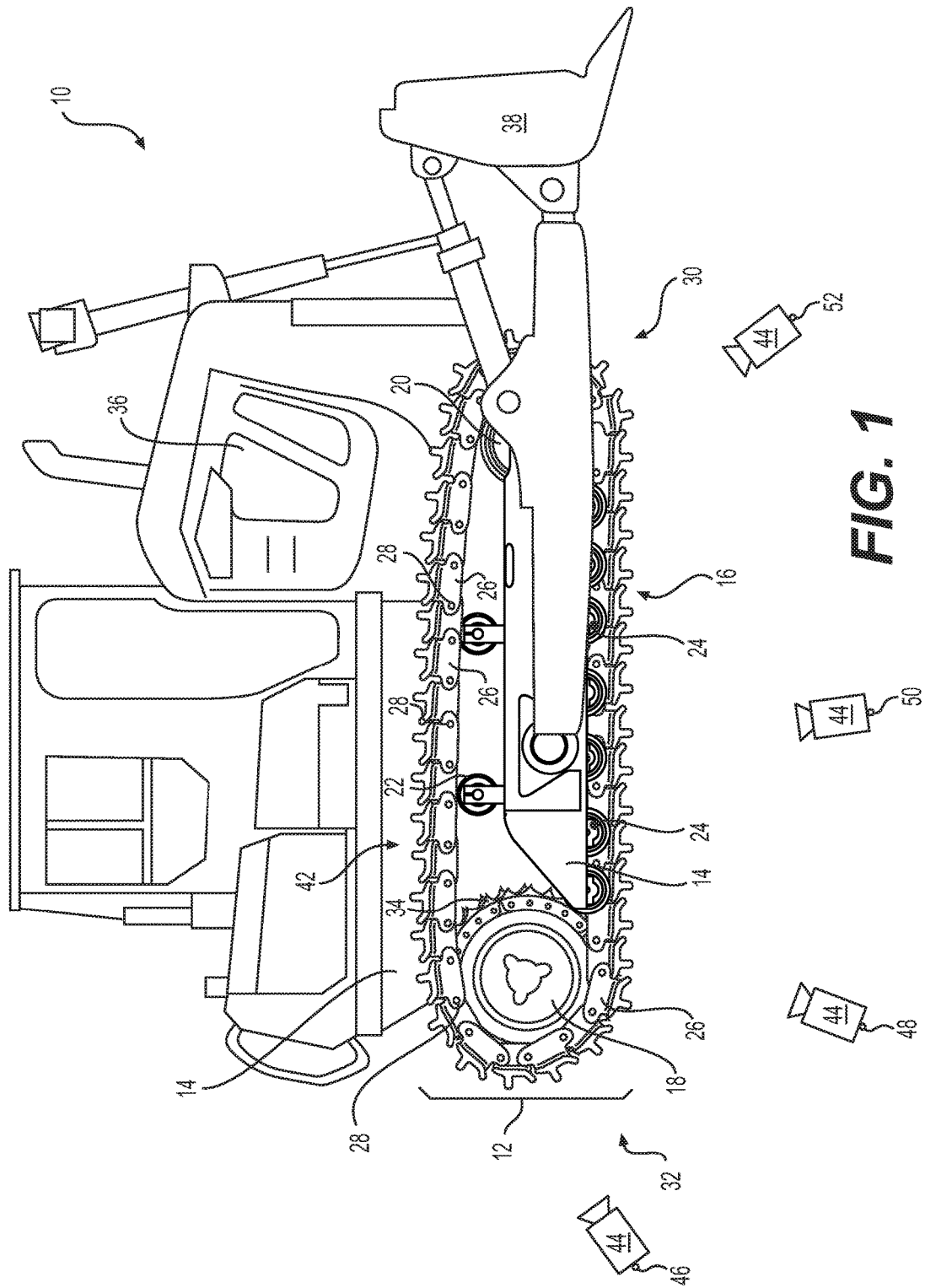
FIG. 1 is a pictorial illustration of an exemplary disclosed machine and an arrangement of imaging devices for obtaining images of the machine.

FIG. 1 illustrates an exemplary embodiment of a machine 10 having an undercarriage 12, which may be used to propel machine 10 in a forward or rearward direction. Machine 10 may perform some type of operation associated with an industry such as construction, mining, or another industry known in the art. For example, as illustrated in FIG. 1, machine 10 may be a loader. It is contemplated however that machine 10 may be an excavator, a tractor, a continuous mining machine, a tank, or another machine having track-type traction devices.

Undercarriage 12 may be configured to support machine 10 and may engage the ground, roads, and/or other types of terrain. Undercarriage 12 may include, among other things, frame 14, track 16, sprocket wheel 18, idler wheel 20, one or more upper rollers 22, and one or more lower rollers 24. In some exemplary embodiments, undercarriage 12 may also include one or more sliders in place of or in addition to upper rollers 22. Sprocket wheel 18, idler wheel 20, upper rollers 22, and lower rollers 24 may be attached to frame 14 of undercarriage 12. Track 16 may wrap around sprocket wheel 18, idler wheel 20, upper rollers 22, and lower rollers 24 to form an endless chain. Track 16 may include a plurality of individual links 26 connected end-to-end via pins 28

Sprocket wheel 18 and idler wheel 20 may be located on opposite ends of undercarriage 12. For example, as illustrated in FIG. 1, idler wheel 20 may be located adjacent front end 30 of frame 14 and sprocket wheel 18 may be located adjacent rear end 32 of frame 14. Sprocket wheel 18 may include one or more projections (or teeth) 34 that engage with track 16 and transfer tractive forces from sprocket wheel 18 to track 16. Sprocket wheel 18 may be rotated by power source 36 of machine 10.

Power source 36 may be an engine, which may generate a power output that can be directed through sprocket wheel 18 and track 16 to propel machine 10 in a forward or rearward direction. For example, power source 36 may be any suitable type of internal combustion engine, such as a gasoline, diesel, natural gas, or hybrid-powered engine. It is also contemplated however that power source 36 may be driven by electrical power. Power source 36 may be configured to deliver power output directly to sprocket wheel 18. Additionally or alternatively, power source 36 may be configured to deliver power output to a generator (not shown), which may in turn drive one or more electric motors (not shown) coupled to sprocket wheel 18. According to yet another embodiment, power source 36 may deliver power output to a hydraulic motor (not shown) fluidly coupled to a hydraulic pump (not shown) and configured to convert a fluid pressurized by the pump into a torque output, which may be directed to sprocket wheel 18. Power source 36 may also provide power to move and/or manipulate work tool 38 associated with machine 10.

Upper and lower rollers 22, 24 may guide track 16 between sprocket wheel 18 and idler wheel 20. For example, upper roller 22 may guide track 16 at an upper track side 40 of frame 14. To do so, upper roller 22 may extend upward from frame 14 and engage an inner portion of links 26. Lower rollers 24 may guide track 16 at a lower track side 42 of frame 14. Lower rollers 24 may each be suspended from frame 14. Lower rollers 24 may ride on and guide links 26 as track 16 travels around sprocket wheel 18 and idler wheel 20.

FIG. 1 also illustrates imaging devices 44, which may be configured to take two-dimensional (2D) images of machine 10 or of undercarriage 12. As illustrated in FIG. 1, imaging device 44 may be located at different positions 46, 48, 50, 52 to allow imaging device 44 to take a plurality of two-dimensional images of machine 10 or of undercarriage 12 from different positions and orientations. Although only four positions 46, 48, 50, 52 are illustrated in FIG. 1, it is contemplated that 2D images of machine 10 or of undercarriage 12 may be obtained from fewer than or more than four positions. Further, although the same imaging device 44 has been shown at each of the positions 46, 48, 50, 52, it is contemplated that different imaging devices 44 could be located at different positions 46, 48, 50, 52 to obtain the plurality of 2D images.

In one exemplary embodiment, imaging device 44 may be a digital camera attached to a movable frame (not shown), which may allow a same imaging device 44 to be moved horizontally and/or vertically around machine 10 to positions 46, 48, 50, 52. Movable frame may also allow imaging device 44 to be rotated, allowing imaging device 44 to be located at different distances and orientations relative to machine 10. In another exemplary embodiment, imaging device 44 may be a digital camera operated by an operator capable of moving to different positions relative to machine 10. The operator may be able to acquire a plurality of 2D images of machine 10 and/or undercarriage 12 from different distances and from different orientations. In yet another exemplary embodiment, imaging device 44 may be a smartphone equipped with a camera, a tablet device equipped with a camera, a computer equipped with a camera, or any other type of electronic equipment known in the art equipped with a camera.

Figure 2:
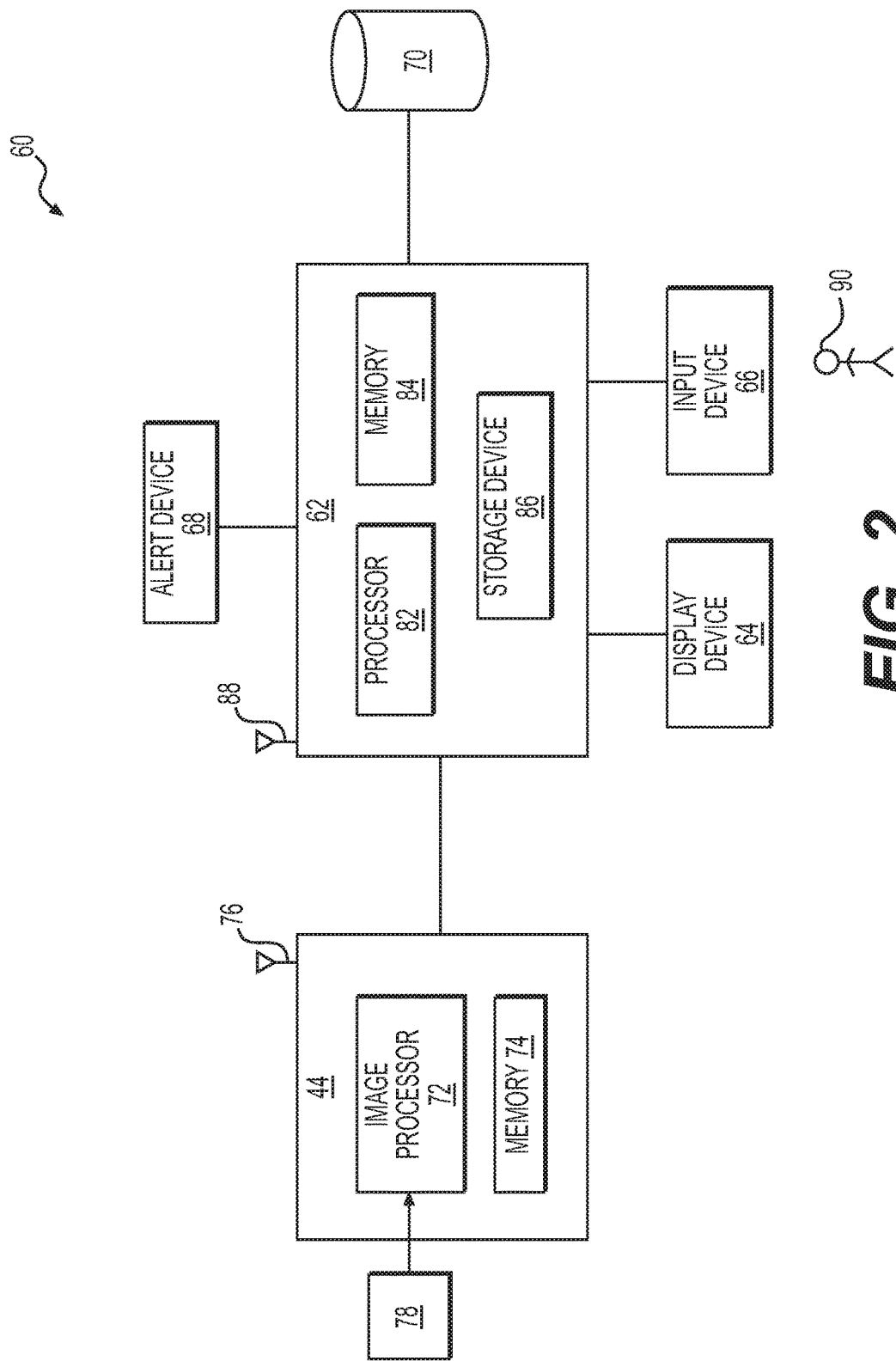
FIG. 2 is a schematic illustration of an exemplary disclosed wear measurement system that may be used with the machine of FIG. 1.

FIG. 2 illustrates a schematic view of an exemplary wear measurement system 60 that may be used with machine 10 or with a machine component, for example, undercarriage 12. Wear measurement system 60 may include imaging device 44, controller 62, display device 64, input device 66, alert device 68, and database 70. Imaging device 44 may include image processor 72, memory 74, and antenna 76. Image processor 72 may be configured to acquire one or more images 78 of a machine component, for example, undercarriage 12, and store images 78 in the form of an electronic data file in memory 74. Images 78 may be two-dimensional still images or may include two-dimensional video images. Image processor 72 may be configured to control antenna 76 to wirelessly transmit the one or more electronic data files representing images 78 to controller 62. Image processor 72 may transmit the one or more images 78 through antenna 76 to controller 62 before or after storing images 78, or even without storing images 78 in memory 74. It is also contemplated that imaging device 44 may transmit or transfer the one or more images 78 to controller 62 through a wired connection or using other ways of transferring digital information known in the art. Although FIG. 2 illustrates only one image processor 72, one memory 74, and one antenna 76, it is contemplated that imaging device 44 may have any number of image processors 72, memories 74, and antennae 76.

Controller 62 may include processor 82, memory 84, storage device 86, and antenna 88. Processor 82 may be configured to control operations of memory 84, storage device 86, and antenna 88. Antenna 88 of controller 62 may be configured to wirelessly receive the one or more images 78 transmitted from imaging device 44 via antenna 76. Memory 84 or storage device 86 may store the images 78 received by antenna 88. Memory 84 or storage device 86 may also store instructions that processor 82 may be configured to execute to perform a variety of operations on images 78 received from imaging device 44. Although FIG. 2 illustrates only one processor 82, one memory 84, one storage device 86, and one antenna 88, it is contemplated that controller 62 may include any number of processors 82, memories 84, storage devices 86, and antennae 88.

Image processor 72 and processor 82 may each embody a single or multiple microprocessors, digital signal processors (DSPs), etc. Numerous commercially available microprocessors can be configured to perform the functions of each of image processor 72 and processor 82. Various other known circuits may be associated with each of image processor 72 and processor 82, including power supply circuitry, signal-conditioning circuitry, and communication circuitry. Memories 74, 84 may embody non-transitory computer-readable media, for example, Random Access Memory (RAM) devices, NOR or NAND flash memory devices, and Read Only Memory (ROM) devices. Storage device 86 may embody non-transitory computer-readable media, such as, RAM, NOR, NAND, or ROM devices, CD-ROMs, hard disks, floppy drives, optical media, solid state storage media, etc.

One or more display devices 64 may be associated with controller 62 and may be configured to display data or information in cooperation with processor 82. For example, display device 64 may be configured to display the one or more 2D images 78 received by controller 62 from imaging device 44. Display device 64 may also be configured to display information generated by processor 82 as a result of operations performed on the one or more images 78. Display device 64 may be a cathode ray tube (CRT) monitor, a liquid crystal display (LCD), a light emitting diode (LED) display, a projector, a projection television set, a touchscreen display, or any other kind of display device known in the art.

One or more input devices 66 may also be associated with controller 62 and may be configured to receive inputs from an operator 90 of wear measurement system 60. Operator 90 may also be capable of operating imaging device 44. It is also contemplated that different operators 90 may operate imaging device 44 and controller 62. Processor 82 may receive inputs from the operator 90 via input device 66 and may perform operations on one or more images 78 based on the received inputs. In one exemplary embodiment, input device 66 may enable an operator 90 of wear measurement system 60 to make selections of one or more portions of the one or more images 78. Input device 66 may also enable the operator to provide numerical, textual, graphic, or audio-visual inputs to processor 82. Input device 66 may include a physical keyboard, virtual touch-screen keyboard, mouse, joystick, stylus, etc. In certain embodiments, input device 66 may also include one or more microphones (not shown) using, for example, speech-to-text and/or voice recognition applications. Although, controller 62, display device 64, input device 66, and database 70 have been described separately, it is contemplated that controller 62, display device 64, input device 66, and database 70 may form a desktop computer system, a server system, a laptop computer system, or any other type of computing system known in the art. It is also contemplated that controller 62, display device 64, input device 66, and database 70 may be part of a server farm consisting of a plurality of servers.

Alert device 68 may be associated with controller 62 and may be configured to generate an audible, a visual, or an audio-visual alert based on instructions received from processor 82. Alert device 68 may be a separate device or may be incorporated in display device 64 to provide audio-visual alerts to operator 90. Database 70 may be associated with controller 62 and may be configured to store instructions for execution by processor 82. Database 70 may also be configured to store the one or more images 78, inputs received from input device 66, and/or images, data, or other information generated as a result of operations performed by processor 82 on the one or more images 78.

INDUSTRIAL APPLICABILITY

The wear measurement system of the present disclosure may be used to perform measurement of components on a wide variety of machines. In particular, the wear measurement system of the present disclosure may be used to obtain two-dimensional images of an entire machine or of a particular component of the machine, and to obtain dimensional measurements using the two-dimensional images without removing the machine from service. The measured dimensions may be compared to specified dimensions to determine amounts of wear on one or more components included in the two-dimensional images. Exemplary methods of operation of wear measurement system 60 will be discussed below.

Figure 3:
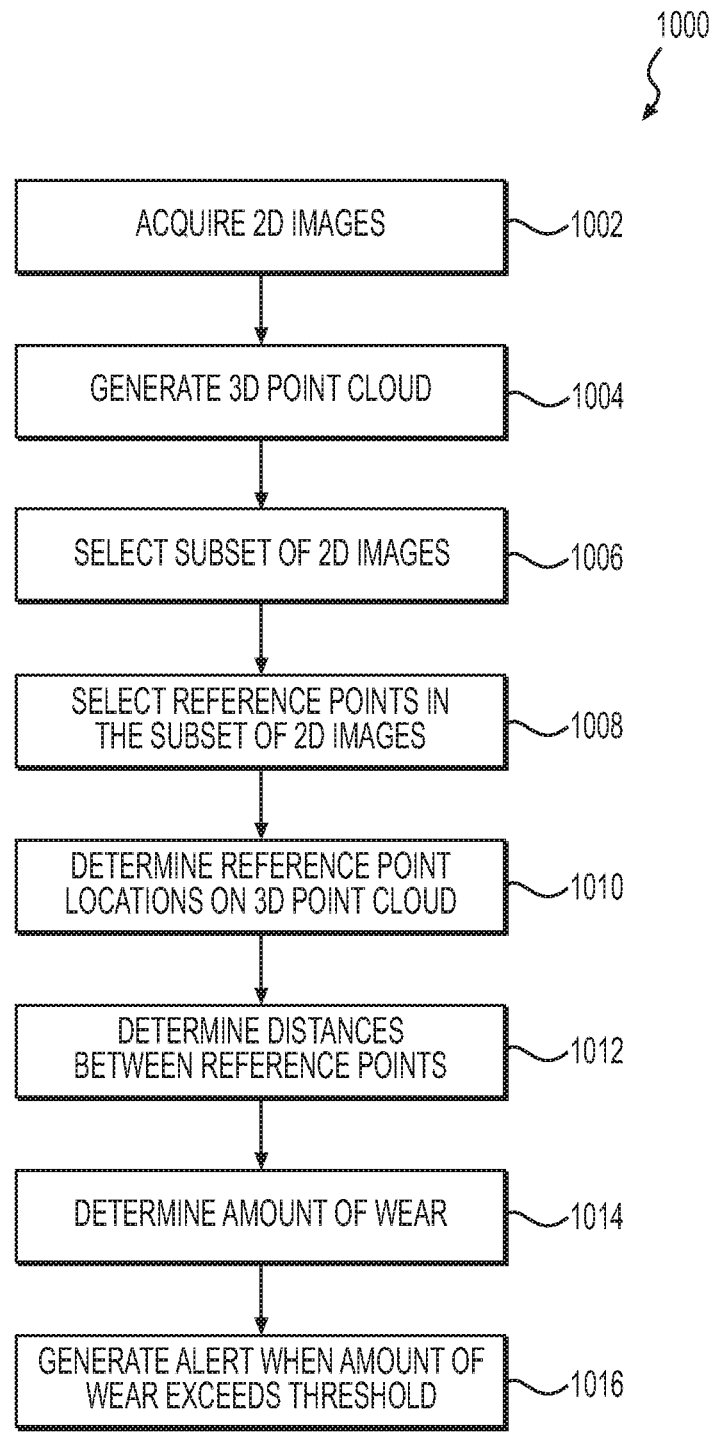
FIG. 3 is a flow chart illustrating an exemplary disclosed wear measurement method performed by the wear measurement system of FIG. 2.

FIG. 3 illustrates an exemplary method 1000 of performing wear measurement on a component, for example, undercarriage 12 of machine 10. For ease of explanation, method 1000 is described with respect to undercarriage 12 of machine 10. One of ordinary skill in the art would recognize however that method 1000 may be similarly applied to any other component of machine 10 or to components of a different machine.

Method 1000 may include a step of acquiring 2D images 78 of a component, such as, undercarriage 12 (Step 1002). As discussed above, imaging device 44 may be used to acquire 2D images 78 of undercarriage 12 from different positions (e.g. positions 46, 48, 50, 52). Further, imaging device 44 may be disposed at different orientations (i.e. rotations with respect to the coordinate axes associated with imaging device 44) at the different positions 46, 48, 50, 52. Images 78 acquired by imaging device 44 may be stored in memory 74 of imaging device 44. It is also contemplated that images 78 may be stored in memory 84 of controller 62 or in database 70. In one exemplary embodiment, each of images 78 may include a two-dimensional view of undercarriage 12. In another exemplary embodiment, images 78 may constitute a two-dimensional video of undercarriage 12, including views from different camera positions or orientations.

Figure 4:
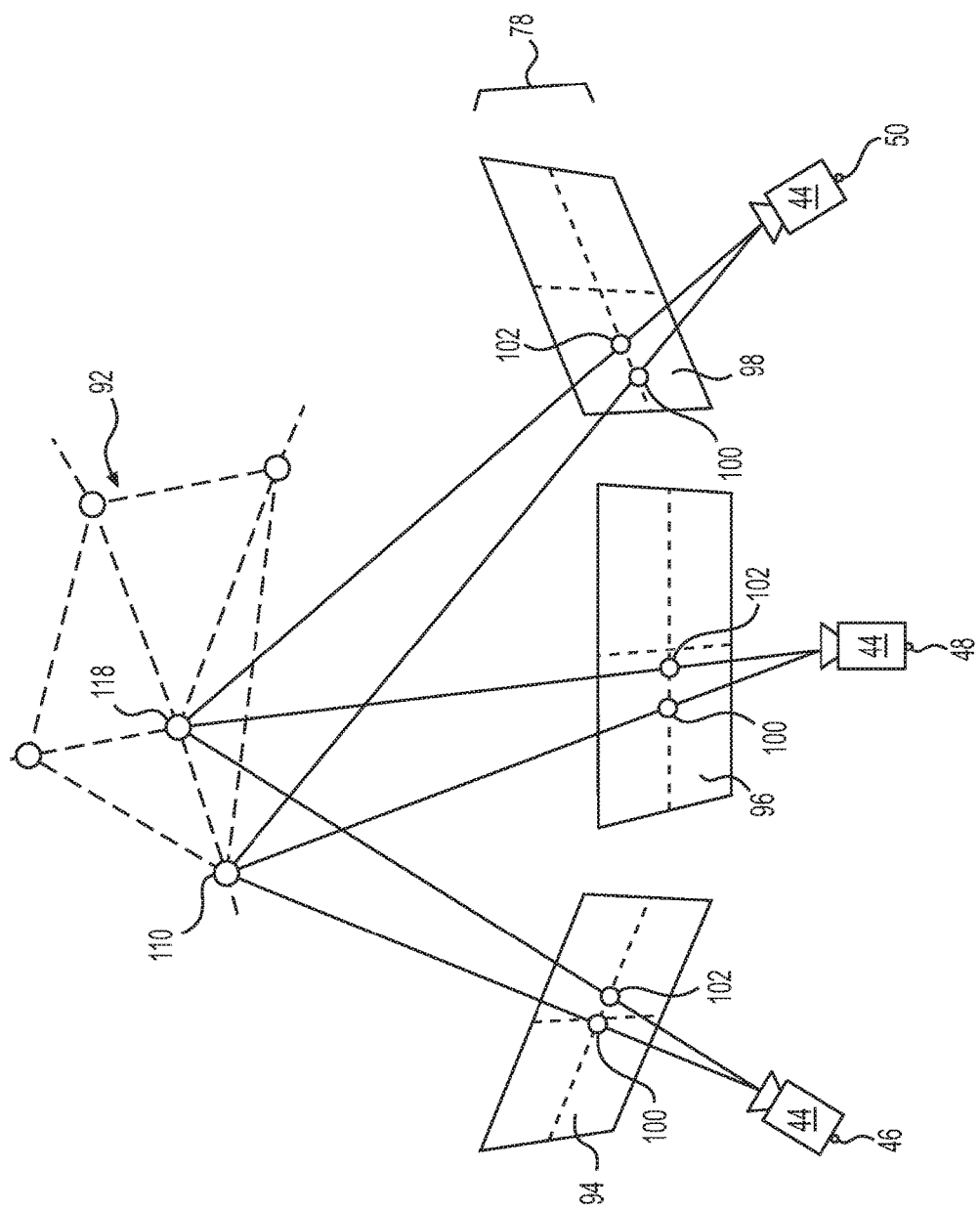
FIG. 4 is a pictorial illustration of an exemplary arrangement for generating a three-dimensional image using two-dimensional images obtained using the wear measurement system of FIG. 2.

Method 1000 may include a step of generating a three-dimensional (3D) image of undercarriage 12 based on 2D images 78 (Step 1004). When images 78 constitute a two-dimensional video, processor 82 of controller 62 may be configured to extract 2D images of undercarriage 12 from the two-dimensional video. FIG. 4 illustrates an exemplary arrangement for generating 3D point cloud 92, using 2D images 78 obtained using imaging device 44. As illustrated in FIG. 4, exemplary 2D images 94, 96, 98 may correspond to positions 46, 48, 50, respectively, of imaging device 44. Processor 82 of controller 62 may be configured to determine positions 46, 48, 50 and orientations of imaging device 44 at each of the positions 46, 48, 50 in a coordinate system associated with wear measurement system 60. Positions 46, 48, 50 and orientations of imaging device 44 may constitute poses of imaging device 44. Processor 82 may determine the poses of imaging device 44 at each of the positions 46, 48, 50 based on a comparison of matching features, such as, 100, 102 that appear in each of 2D images 94, 96, 98. Processor 82 may determine the poses by comparing the relative positions of features 100, 102 in 2D images 94, 96, 98. Processor 82 may determine the positions of features 100, 102 in 2D images 94, 96, 98 using triangulation techniques. In one exemplary embodiment, processor 82 may sequentially refine the positions of features 100, 102 in 2D images 94, 96, 98, by updating the positions as each 2D image is processed.

Matching features 100, 102 may be selected in many different ways. In one exemplary embodiment, an operator 90 of wear measurement system 60 may view images 94, 96, 98 on display device 64 and use one or more input devices 66 to identify and select matching features 100, 102 in each of 2D images 94, 96, 98. For example, operator 90 may use a mouse to select matching features 100, 102 in each of 2D images 94, 96, 98. Matching features 100, 102 may include one or more distinguishable features of the imaged component. For example, in 2D images 94, 96, 98 of undercarriage 12, matching features 100, 102 may include pins 28 connecting adjacent links 26 of track 16, sprocket wheel 18, idler wheel 20, upper and/or lower rollers 22, 24, etc.

In another exemplary embodiment, processor 82 may use feature matching algorithms to automatically identify and select matching features 100, 102 in each of 2D images 94, 96, 98. For example, processor 82 may perform a comparison of a portion of or an entirety of images 94, 96, 98 with images of features 100, 102 stored in memory 84, storage device 86, and/or database 70 to identify features 100, 102 in each of 2D images 94, 96, 98.

In step 1004 of method 1000, processor 82 of controller 62 may generate point cloud image 92 using triangulation and optimization techniques. For example, processor 82 may generate point cloud image based on the poses (positions and orientations) of imaging devices 44 and the relative positions of matching features 100, 102 in 2D images 94, 96, 98.

Although FIG. 4 illustrates only three images 94, 96, 98 at three positions 46, 48, 50, and only two matching features 100, 102, it is contemplated that any number of images 78 at any number of positions (e.g. 46, 48, 50), and any number of features (e.g. 100, 102) may be used to generate 3D point cloud 92 using 2D images 78. One of ordinary skill in the art would recognize that locations 110, 118, etc. in 3D point cloud 92 may appear as point representations of features 100, 102, respectively. One of ordinary skill in the art would also recognize that 3D point cloud 92 may not include continuous edges, but may instead include a cluster of locations representing discrete reference points in 2D images 78. As a result 3D point cloud 92 may be an image that includes a cloud of points representing locations of discrete reference points in 2D images 78.

Returning to FIG. 3, method 1000 may include a step of selecting a subset of 2D images 78 from the plurality of images 78 of undercarriage 12 obtained by imaging device 44 (Step 1006). In one exemplary embodiment, operator 90 may view each of the plurality of images 78 on display device 64 and use input device 66 to select the subset of images 78. For example, the plurality of 2D images 78 may include more than fifty images and operator 90 may select a subset of four 2D images 78 from the more than fifty 2D images 78. In another exemplary embodiment, processor 82 may use, for example, a randomization algorithm to randomly select a subset of 2D images 78 from the plurality of images 78.

Figure 5:
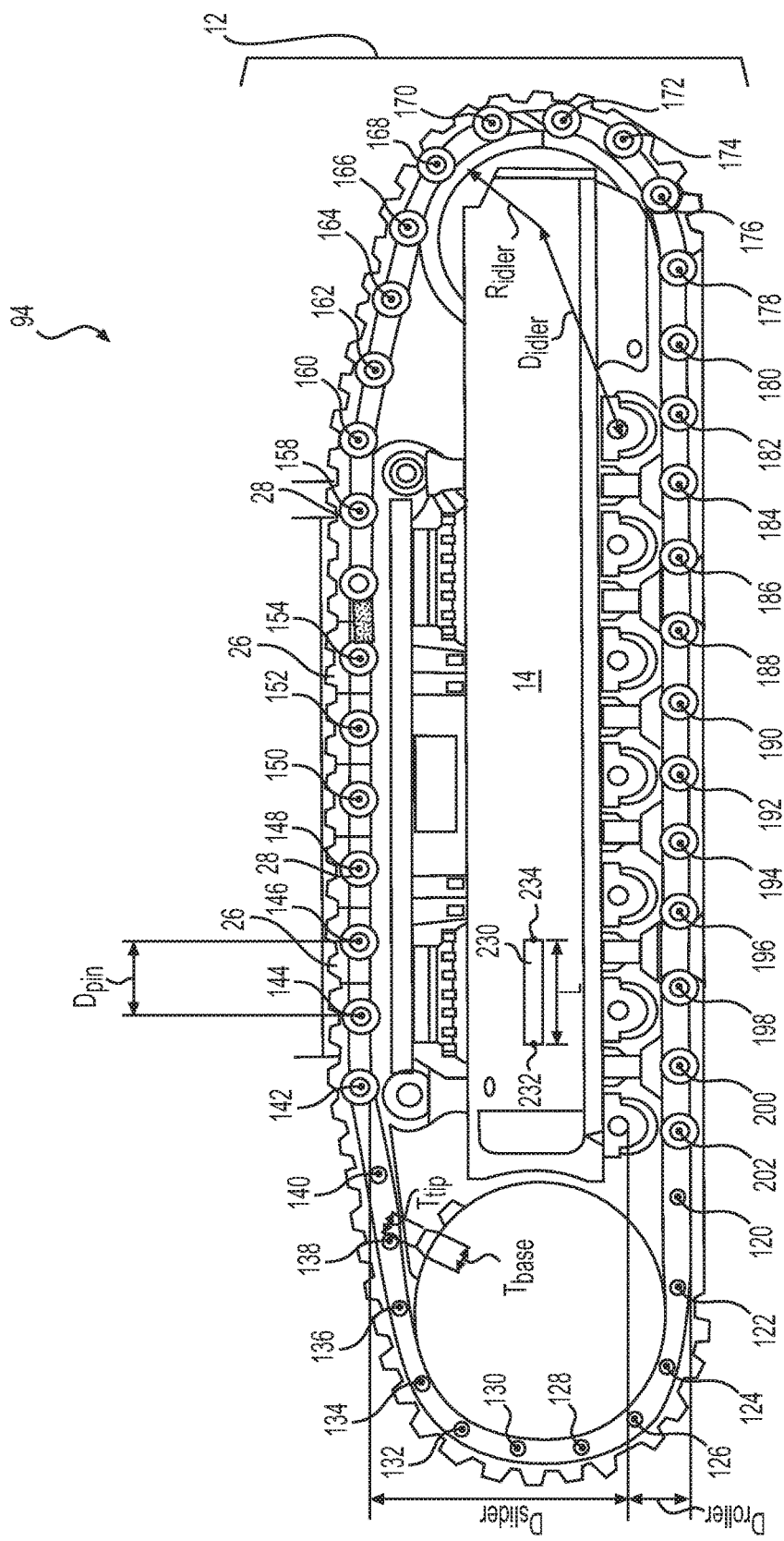
FIG. 5 is a pictorial illustration of an exemplary two-dimensional image obtained using the wear measurement system of FIG. 2.

Method 1000 may include a step of selecting reference points in the subset of 2D image 78 (Step 1008). In one exemplary embodiment, operator 90 may view each of the subset of 2D images 78 on display device 64 and use input device 66, to identify and select reference points on each of the subset of 2D images 78. FIG. 5 illustrates an exemplary 2D image 94 from the subset of 2D images 78 of undercarriage 12 selected by operator 90. As illustrated in FIG. 5, operator 90 may select, for example, center points 120-202 of pins 28 that connect adjacent links 26 of undercarriage 12. Operator 90 may identify and select center points 120-202 of pins 28 on each of the subset of 2D images 78 selected, for example, in step 1006. It is contemplated that operator 90 may select any number of reference points in each of the subset of 2D images 78.

Figure 6:
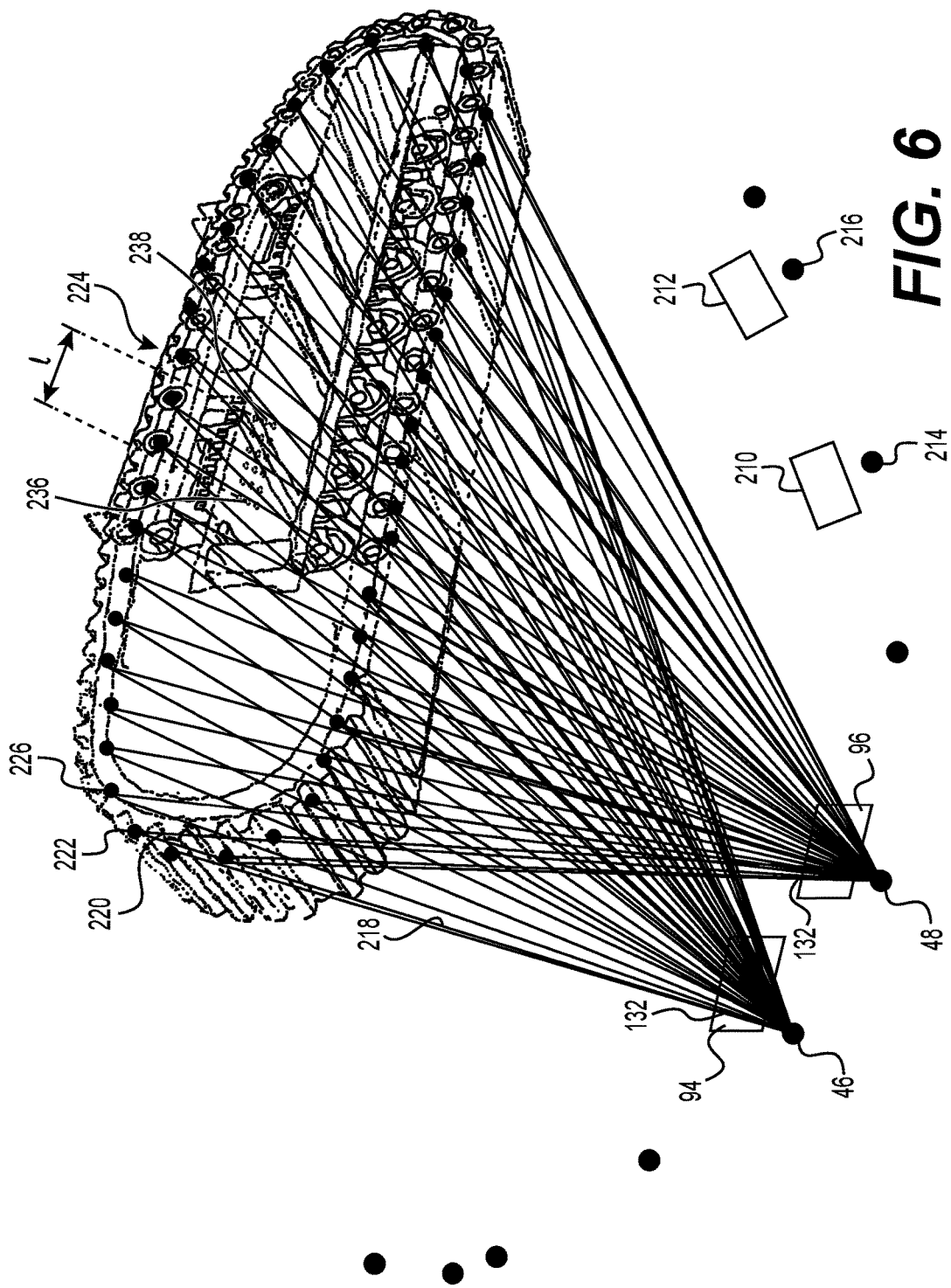
FIG. 6 is a pictorial illustration of the exemplary locations of the reference points of FIG. 5 projected on the three-dimensional image of FIG. 4.

Returning to FIG. 3, method 1000 may include a step of determining reference point locations on 3D point cloud 92 (Step 1010) generated, for example, in step 1004. FIG. 6 illustrates a subset of four 2D images 94, 96, 210, 212 and the associated positions 46, 48, 214, 216, of imaging device 44 for each of the four images 94, 96, 210, 212, respectively. Processor 82 may project lines from each of positions 46, 48, 214, 216 through reference points 120-202 in each of the associated 2D images 94, 96, 210, 212, respectively. Thus, for example, processor 82 may project ray 218 from position 46 through reference point 132 (see also FIG. 5) in 2D image 94. Processor 82 may similarly project ray 220 from position 48 through reference point 132 in 2D image 96. Processor 82 may repeat this process for 2D images 210, 212. Processor 82 may determine, for example, location 222 of reference point 132 on 3D point cloud 224 based on an intersection of rays 218, 220 and similar rays from positions 214, 216 corresponding to 2D images 210, 212, respectively. Because of potential differences in imaging conditions for images 94, 96, 210, 212 and inherent errors associated with imaging objects, rays 218, 220 and rays from positions 214, 216 passing through reference point 132 may not converge at a single location 222 in three-dimensional space. In such cases, processor 82 may determine location 222 of reference point 132 in 3D point cloud 224 as the position where a measure of distance between rays 218, 220 and rays from positions 214, 216 passing through reference point 132 is less than a threshold distance. Processor 82 may repeat these steps for each of the reference points 120-202 (see FIG. 5) to determine the locations of each of the reference points 120-202 in 3D point cloud 224.

Returning to FIG. 3, method 1000 may include a step of determining distances between the reference points 120-202 (Step 1012). Processor 82 may determine locations (e.g. 222, 226) in 3D point cloud 224 (see FIG. 6) that are representative of reference points (e.g. 132, 134 in FIG. 5). Processor 82 may further determine an image distance between the locations (e.g. 222, 226). As used in this disclosure, image distance represents a distance between locations on a 3D point cloud (e.g. 224). One of ordinary skill in the art would recognize that image distance would depend on the dimensions of the 3D point cloud. One of ordinary skill in the art would also recognize that image distance would be different from an actual distance between the reference points on an actual undercarriage 12 of machine 10. In one exemplary embodiment, processor 82 may determine the image distance as a number of pixels located between the locations (e.g. 222, 226 in FIG. 6)

corresponding to reference points (e.g. 132, 134 in FIG. 5). In another exemplary embodiment, processor 82 may determine the image distance in physical dimensions (mm, cm, etc.) between the locations (e.g. 222, 226 in FIG. 6) corresponding to the reference points (e.g. 132, 134 in FIG. 5) based on, for example, dimensions of display device 64 or a size of pixels in display device 64. Processor 82 may also be configured to determine a scaling factor "S" to convert the image distance into an actual distance that would be observed on undercarriage 12.

Processor 82 may determine the scaling factor S in a variety of ways. In one exemplary embodiment, processor 82 may determine the scaling factor S based on the known dimensions of a feature 230 (see FIG. 5), which may exist on undercarriage 12. For example, as illustrated in FIG. 5, frame 14 of undercarriage 12 may include an embossed feature 230 of known length "L" extending between reference points 232, 234. Processor 82 may identify the locations 236, 238 (see FIG. 6) of reference points 232, 234, on either end of the embossed feature 230, in 3D point cloud 224 in a manner similar to that described above with respect to reference points 120-202. Processor 82 may determine image distance "l" between locations 236, 238 on 3D point cloud 224, corresponding to the reference points 232, 234. Processor 82 may use the known length L of the embossed strip 230 and image distance l to determine the scaling factor S (e.g. S=L/l).

In another exemplary embodiment, a linear scale (e.g. tape measure) may be placed on frame 14 of undercarriage 12 before acquiring the 2D images 78. Operator 90 may identify two reference points on an image of the tape measure in step 1008 of method 1000. Processor 82 may determine the image distance between the locations in 3D point cloud 224 corresponding to the two reference points on the tape measure. Processor 82 may determine the scaling factor S based on the determined image distance and a known length of the tape measure between the two reference points selected by operator 90. Processor 82 may use the scaling factor S to determine an actual distance that would be observed on an actual undercarriage 12.

Figure 7:
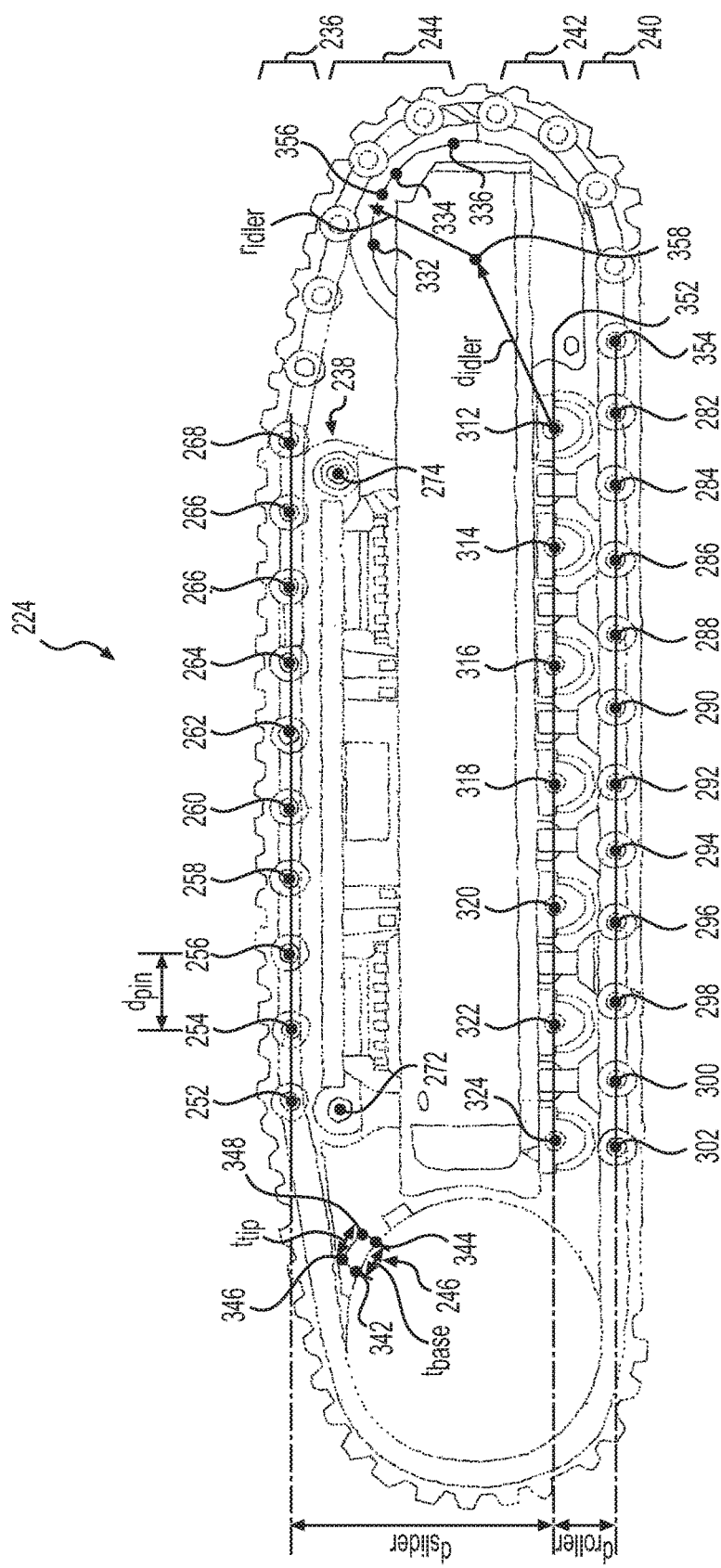
FIG. 7 is a pictorial illustration of an exemplary disclosed undercarriage overlaid with locations of reference points used for making exemplary dimensional measurements.

FIG. 7 illustrates an exemplary 3D point cloud 224, showing locations that may be used to determine physical dimensions of an undercarriage 12. For example, six sets 236-246 of locations are illustrated in FIG. 7. Set 236 may include locations 252-268, corresponding to center points of pins 28 on upper track side 40 of undercarriage 12. Set 238 may include locations 272, 274, corresponding to center points of two upper rollers 22. Set 240 may include locations 282-302, corresponding to center points of pins 28 on lower track side 42 of undercarriage 12. Set 242 may include locations 312-324, corresponding to center points of lower rollers 24. Set 244 may include locations 332, 334, 336, corresponding to three reference points on idler wheel 20 of undercarriage 12. Set 246 may include locations 342-348, corresponding to reference points on tooth 34 of sprocket wheel 18.

One of ordinary skill in the art would recognize that locations 252-268, 272, 274, 282-302, 312-324, 332-336, and 343-348 may correspond to reference points selected in step 1008 as discussed above with respect to FIG. 5. For example, locations 252-268 of set 236 in 3D point cloud 224 may correspond with reference points 142-160 in 2D image 94 shown in FIG. 5. Similarly, for example, locations 282-302 of set 240 in 3D point cloud 224 may correspond to reference points 182-202 in 2D image 94. Processor 82 may determine actual distances, for example, pin center-to-center distance "$D_{pin}$," slider distance "$D_{slider}$," roller distance "$D_{roller}$," idler radius "$R_{idler}$," idler location "$D_{idler}$," and drive tooth thicknesses "$T_{base}$," and "$T_{tip}$" (see FIG. 5) based on the six sets 236-246 of locations 252-268, 272, 274, 282-302, 312-324, 332-336, and 343-348 in 3D point cloud 224.

As illustrated in FIG. 5, $D_{pin}$ may represent a distance between the center points of adjacent pins (e.g. 142, 144). Processor 82 may determine dimension $D_{pin}$ by measuring an image distance $d_{pin}$ between locations (e.g. 254, 256 selected from set 236 in FIG. 7) representing adjacent pairs of center points (e.g. 142, 144 in FIG. 5). Processor 82 may use scaling factor S to convert image distance $d_{pin}$ to actual distance $D_{pin}$ (e.g. $D_{pin}=S \times d_{pin}$).

To determine dimension $D_{slider}$ (see FIG. 5), processor 82 may fit a straight line 350 through locations 252-268 in set 230 and a straight line 352 through locations 312-324 in set 236 of 3D point cloud 224 (see FIG. 7). Processor 82 may determine an image distance $d_{slider}$, for example, as a perpendicular distance between straight lines 350 and 352. Processor 82 may convert image distance $d_{slider}$ into an actual distance $D_{slider}$ using the scaling factor S (e.g. $D_{slider}=S \times d_{slider}$).

Similarly, to determine $D_{roller}$, processor 82 may fit a straight line 352 through locations 312-324 in set 236 and straight line 354 through locations 282-302 in set 234 of 3D point cloud 224. Processor 82 may determine an image distance $d_{roller}$, for example, as a perpendicular distance between straight lines 352 and 354. Processor 82 may convert image distance $d_{roller}$ into an actual distance $D_{roller}$, using the scaling factor S (e.g. $D_{roller}=S \times d_{roller}$).

As further illustrated in FIG. 7, to determine radius of idler wheel 20, $R_{idler}$, processor 82 may fit a circle 356 that passes through locations 332-336 in set 238 of 3D point cloud 224 (see FIG. 7). Processor 82 may determine image distance $r_{idler}$ as a radius of the fitted circle 356 and use the scaling factor S to convert image distance $r_{idler}$ to actual distance $R_{idler}$ (e.g. $R_{idler}=S \times r_{idler}$). Processor 82 may also determine a distance, $D_{idler}$, of idler wheel 20 from a lower roller 24 by determining an image distance $d_{idler}$ between location 312 and a center 358 of the fitted circle 356 in 3D point cloud 224 (see FIG. 7). Processor 82 may convert image distance $d_{idler}$ into actual distance using the scaling factor S (e.g. $D_{idler}=S \times d_{idler}$).

Similarly, processor 82 may determine image distances $t_{base}$ and $t_{tip}$ as the distances between locations 342, 344 and 346, 348, respectively in 3D point cloud 224. Processor 82 may convert image distances $t_{base}$ and $t_{tip}$ into actual thickness $T_{base}$ at a base of tooth 34 and actual thickness $T_{tip}$ at a tip of tooth 34, using scaling factor S (e.g. $T_{base}=S \times t_{base}$ and $T_{tip}=S \times t_{tip}$).

Returning to FIG. 3, method 1000 may include a step of determining an amount of wear (Step 1014). Processor 82 may determine amounts of wear by comparing the actual distances determined in, for example, step 1012 with specified values of the corresponding dimensions. For example, the dimensions $D_{pin}$, $D_{slider}$, $D_{roller}$, $R_{idler}$, $D_{idler}$, $T_{base}$, and $T_{tip}$ may have specified values $D_{pin-S}$, $D_{slider-S}$, $D_{roller-S}$, $R_{idler-S}$, $D_{idler-S}$, $T_{base-S}$, and $T_{tip-S}$. Processor 82 may determine an amount of wear as a difference between the actual distances determined, for example, in step 1012 and the specified values. For example, an amount of pin wear $\Delta_{pin}$ may be determined by processor 82 as a difference between $D_{pin-S}$ and $D_{pin}$ (i.e. $D_{pin-S}-D_{pin}$). Processor 82 may similarly determine an amount of slider wear $\Delta_{slider}$ (i.e. $D_{slider-S}-D_{slider}$), an amount of roller wear $\Delta_{roller}$ (i.e. $D_{roller-S}-D_{roller}$), an amount of idler wear $\Delta_{idler}$ (i.e. $R_{idler-S}-R_{idler}$), an amount of wear in idler location $\Delta_{idler-loc}$ (i.e. $D_{idler-S}-$ $D_{idler}$), and amounts of drive tooth wear $\Delta_{base}$ (i.e. $T_{base-S}-T_{base}$) and $\Delta_{tip}$ (i.e. $T_{tip-S}-T_{tip}$). Although a simple difference between two values to determine an amount of wear is discussed above, it is contemplated that processor 82 may use ratios, absolute values, or any other mathematical functions or operations on the actual distances and the corresponding specified values to determine the amounts of wear. It is contemplated that operator 90 may identify and select fewer than or more than six sets 236-246 of locations 252-268, 272, 274, 282-302, 312-324, 332-336, and 343-348 in, for example, step 1008 of method 1000. It is further contemplated that processor 82 may determine fewer than or more than the actual distances $D_{pin}$, $D_{slider}$, $D_{roller}$, $R_{idler}$, $D_{idler}$, $T_{base}$, and $T_{tip}$, discussed above.

Method 1000 may also include a step of generating an alert when an amount of wear exceeds a threshold amount (Step 1016). Processor 82 may compare one or more amounts of wear $\Delta_{pin}$, $\Delta_{slider}$, $\Delta_{roller}$, $\Delta_{idler}$, $\Delta_{idler-loc}$, $\Delta_{base}$, and $\Delta_{tip}$ with their respective threshold amount of wear $\Delta_{pin-limit}$, $\Delta_{slider-loc}$, $\Delta_{roller-limit}$, $\Delta_{idler-limit}$, $\Delta_{idler-loc-limit}$, $\Delta_{base-limit}$, and $\Delta_{tip-limit}$, respectively. When a determined amount of wear ($\Delta_{pin}$, $\Delta_{slider}$, $\Delta_{roller}$, $\Delta_{idler}$, $\Delta_{idler-loc}$, $\Delta_{base}$, or $\Delta_{tip}$) exceeds a corresponding threshold amount ($\Delta_{pin-limit}$, $\Delta_{slider-limit}$, $\Delta_{roller-limit}$, $\Delta_{idler-limit}$, $\Delta_{idler-loc-limit}$, $\Delta_{base-limit}$, and $\Delta_{tip-limit}$), processor 82 may signal alert device 68 to generate an alert, which may be audible, visual, or both. It is also contemplated that operator 90 may use the one or more amounts of wear $\Delta_{pin}$, $\Delta_{slider}$, $\Delta_{roller}$, $\Delta_{idler}$, $\Delta_{idler-loc}$, $\Delta_{base}$, and $\Delta_{tip}$ to determine when to order replacement parts or when to schedule maintenance activities for machine 10. Thus, by determining amounts of wear without taking machine 10 out of service, method 1000 may allow operator 90 to schedule and perform maintenance on machine 10 in a more timely and cost effective manner.

Figure 8:
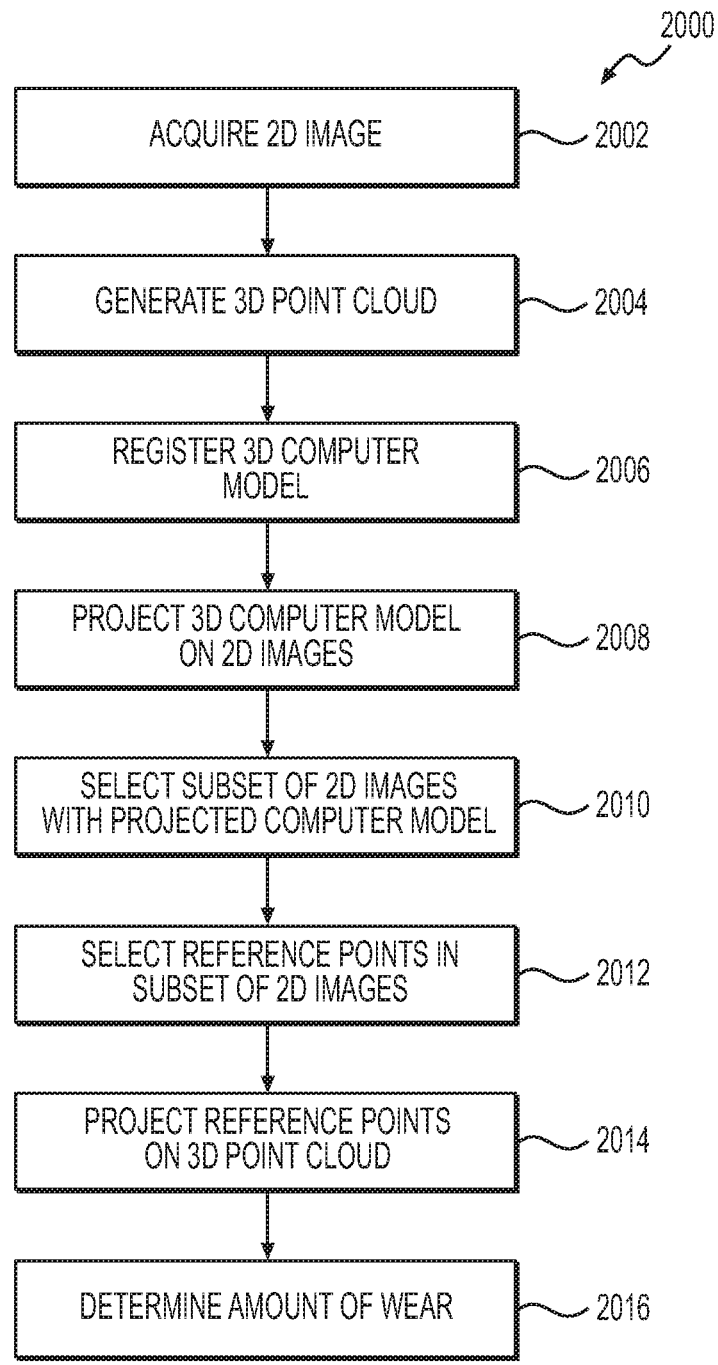
FIG. 8 is flow chart illustrating another exemplary disclosed wear measurement method performed by the wear measurement system of FIG. 2.

FIG. 8 illustrates another exemplary method 2000 of performing wear measurement on a component, for example, undercarriage 12 of machine 10. For ease of explanation, in the following, method 2000 is described with respect to wear measurement on undercarriage 12 of machine 10. One of ordinary skill in the art would recognize however that method 2000 may be similarly applied to any other component of machine 10 or to components of a different machine.

Method 2000 may include a step of acquiring one or more 2D images 78 of a component, such as, undercarriage 12 (Step 2002). Imaging device 44 and processor 82 may perform operations similar to those discussed above with respect to, for example, step 1002 of method 1000 to acquire 2D images 78 of undercarriage 12. Method 2000 may also include a step of generating a 3D point cloud 224 of undercarriage 12 based on the 2D images 78 (Step 2004). Processor 82 may perform operations similar to those discussed above with respect to, for example, step 1002 of method 1000 to generate 3D point cloud 224.

Method 2000 may include a step of registering a three-dimensional computer model with 3D point cloud 224 (Step 2006). In one exemplary embodiment, the computer model may include a computer-aided-design (CAD) representation of undercarriage 12. Processor 82 may overlay the 3D computer model of undercarriage 12 on 3D point cloud 224 generated in, for example, step 2004. Processor 82 may select a first set of register points in the 3D computer model. For example, the first set of register points may include the center points of sprocket wheel 18, idler wheel 20, pins 28, upper rollers 22, lower rollers 24, etc. Processor 82 may select a second set of register points corresponding to the first set of register points in 2D images 78. For example, processor 82 may select center points of sprocket wheel 18, idler wheel 20, pins 28, upper rollers 22, lower rollers 24, etc., in 2D images 78 as the second set of register points. Processor 82 may project the second set of register points on the 3D point cloud using operations similar to those discussed above with respect to step 2004. Processor 82 may orient (i.e. scale and/or rotate) 3D point cloud 224 such that the first set of register points in the computer model overlap the locations corresponding to the second set of register points in 3D point cloud 224. In another exemplary embodiment, processor 82 may orient (i.e. scale and/or rotate) the 3D computer model such that the first set of register points in the computer model overlap the locations corresponding to the second set of register points in 3D point cloud 224. In one exemplary embodiment, the first set of register points and the second set of register points may each include at least four locations.

Figure 9:
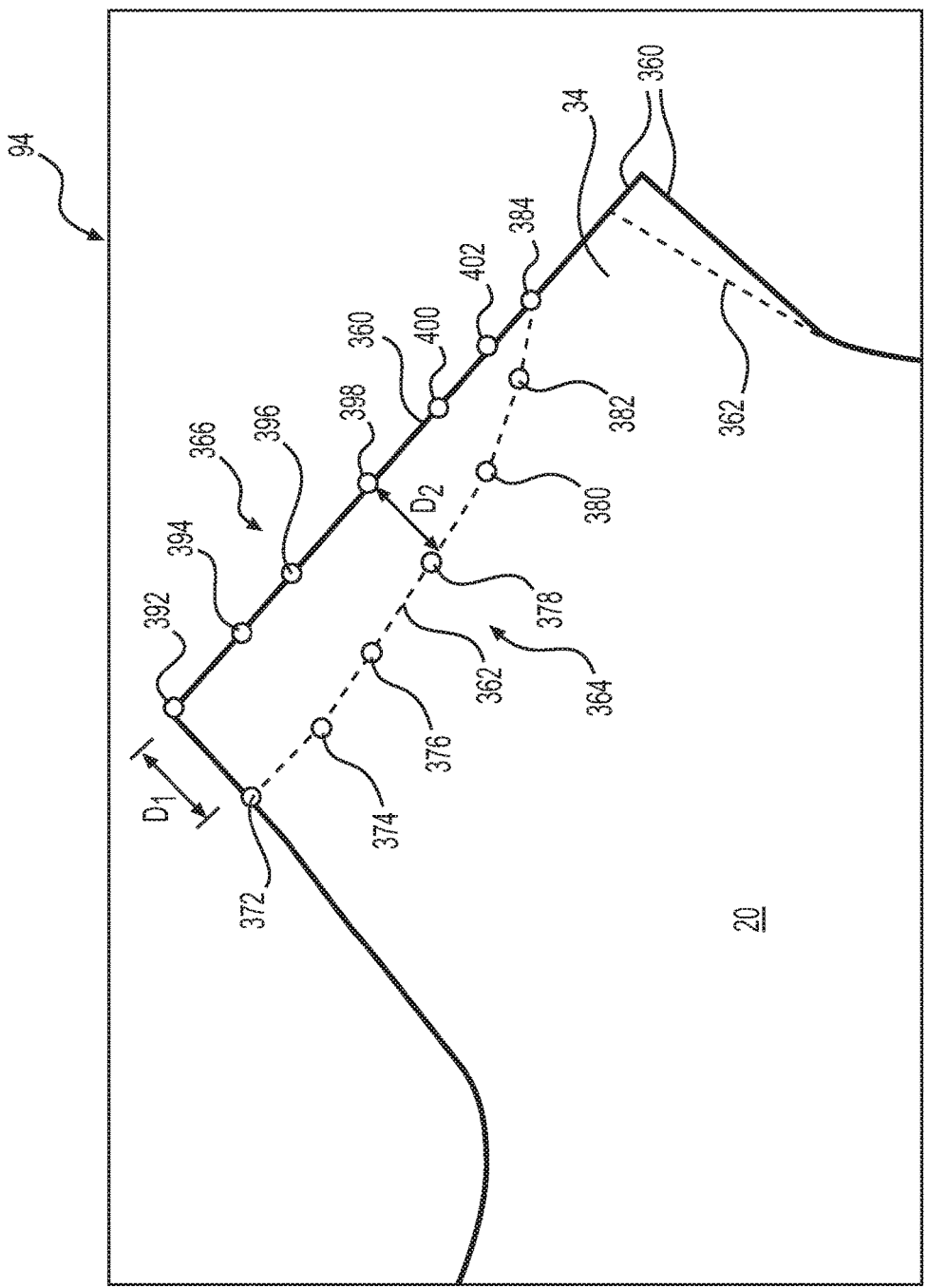
FIG. 9 is a pictorial illustration of exemplary reference points for making dimensional measurement using a computer model.

Method 2000 may include a step of projecting the 3D computer model onto 2D images 78 (Step 2008) obtained, for example, in step 2002. In one exemplary embodiment, processor 82 may project the 3D computer model image on a subset of 2D images 78 based on the position and orientation (pose) associated with each 2D image relative to the 3D point cloud 224 of undercarriage 12. For example, referring to FIG. 6, processor 82 may project the computer model onto each of 2D images 94, 96, 210, 212 based on their positions 46, 48, 214, 216, respectively, and the orientations of imaging device 44 at positions 46, 48, 214, 216. FIG. 9 illustrates a magnified view of a portion of an exemplary 2D image 94 that includes a projection of the 3D computer model. As illustrated in FIG. 9, edge 360 of the computer model illustrates the as-designed shape of tooth 34 on sprocket wheel 18 of undercarriage 12. Edges 362 in FIG. 9 represent the actual shape of tooth 34 as observed in 2D image 94.

Returning to FIG. 8, method 2000 may include a step of selecting a subset of 2D images 78 with the projected computer model (Step 2010). In step 2010, processor 82 may perform operations similar to those discussed above with respect to, for example, step 1006 of method 1000. Method 2000 may also include a step of selecting reference points in the subset of 2D images 78 (Step 2012). In one exemplary embodiment, operator 90 may view each of the subset of 2D images 78 including a projection of the computer model on display device 64 and use input device 66, to identify and select reference points for making wear measurements on each of the subset of 2D images 78. As illustrated in FIG. 9, operator 90 may select, for example, two sets 364 and 366 of reference points in 2D image 94. For example, operator 90 may select set 364 of reference points 372-384 located on an outline of tooth 34 of sprocket wheel 18 as visible in 2D image 94 obtained using imaging device 44. Operator 90 may also select set 366 of reference points 392-402 located on the as-designed edge 360 of tooth 34 as seen in the projection of the computer model. Operator 90 may similarly select sets 364 and 366 of reference points on other 2D images (e.g. 96, 98) included in the subset of 2D images 78.

Returning to FIG. 8, method 2000 may include a step of projecting reference points on 3D point cloud 224. For example, processor 82 may project rays from positions (e.g. 46, 48, 50) through reference points 372-384 and 392-402 in 2D images (e.g. 94, 96, 98). Processor 82 may determine locations corresponding to reference points 372-384 and 392-402 on 3D point cloud 224 based on intersection of the rays using operations similar to those discussed above with respect to, for example, step 1010 of method 1000.

Method 2000 may also include a step of determining amounts of wear (Step 2016). For example, processor 82 may determine an image distance "$d_1$" between locations corresponding to, for example, reference points 372 and 392 (see FIG. 10) on 3D point cloud 224. Similarly, for example, processor 82 may be configured to determine an image distance "$d_2$" between locations corresponding to, for example, reference points 378 and 398 (see FIG. 10) on 3D point cloud 224. Processor 82 may also be configured to convert image distances $d_1$ and $d_2$ into amounts of wear $\Delta_1$ and $\Delta_2$ based on a scaling factor S (e.g. $\Delta_1 = S \times d_1$ and $\Delta_2 = S \times d_2$). One of ordinary skill in the art would recognize that when 3D point cloud 244 is scaled/rotated in step 2006, image distances $d_1$ and $d_2$ would be identical to amounts of wear $\Delta_1$ and $\Delta_2$, and scaling factor S may be 1. One of ordinary skill in the art would also recognize that when the 3D computer model is scaled/rotated in step 2006, image distances $d_1$ and $d_2$ may be different from the amounts of wear $\Delta_1$ and $\Delta_2$ and scale factor S may be different from 1.

Processor 82 may be configured to determine scaling factor S in a variety of ways. In one exemplary embodiment, processor may determine the scaling factor S based on the known dimensions of a feature 340, which may exist on undercarriage 12, by performing processes similar to those discussed above with respect to, for example, step 312 of method 1000. In another exemplary embodiment, processor 82 may determine the scaling factor based on the known distance between two reference points in the computer model. For example, referring to FIG. 9, processor may determine scaling factor based on a distance between reference points 392 and 402. Because reference points 392 and 402 lie on the computer model outline 360 of tooth 34, processor 82 may determine a model distance "W" between reference points 392 and 402 based on the computer model. Processor 82 may also determine a reference image distance "w" between locations corresponding to reference points 392 and 402 in 3D point cloud 224. Processor 82 may determine scaling factor S based on the model distance W and the reference image distance w (e.g. $S = W/w$).

Processor 82 may be also configured to compare the amounts of wear $\Delta_1$ and $\Delta_2$ to a threshold amount of wear to determine whether sprocket wheel 18 requires repair or replacement. It is also contemplated that processor 82 may determine a single value representing the amount of wear by averaging, taking the maximum of, or performing any other mathematical operations on the individual amounts of wear $\Delta_1$, $\Delta_2$, etc. Thus, by determining the amounts of wear without taking machine 10 out of service, method 2000 may allow operator 90 to schedule and perform maintenance on machine 10 in a more timely and cost effective manner. For example, operator 90 may use processor 82 to determine an amount of time "$t_{life}$," after which amounts of wear $\Delta_1$, $\Delta_2$, etc. may exceed a threshold amount of wear $\Delta_{limit}$. One of ordinary skill in the art would recognize that $t_{life}$, may represent a remaining useful life of a particular component, for example, sprocket wheel 18 on machine 10. Operator 90 may procure replacement parts and/or schedule maintenance for machine 10 based on the determined amount of time $t_{life}$. Thus, operator 90 may be able to help ensure that machine 10 is not scheduled for maintenance too far in advance of the remaining useful life $t_{life}$ or at a time that exceeds $t_{life}$.

It will be apparent to those skilled in the art that various modifications and variations can be made to the disclosed wear measurement system without departing from the scope of the disclosure. Other embodiments of the wear measurement system will be apparent to those skilled in the art from consideration of the specification and practice of the wear measurement system disclosed herein. It is intended that the specification and examples be considered as exemplary only, with a true scope of the disclosure being indicated by the following claims and their equivalents.

What is claimed is:

1. A wear measurement system for a component, comprising:
    an imaging device configured to obtain a plurality of two-dimensional images of the component; and
    a controller configured to:
        generate a three-dimensional point cloud representing the component based on the two-dimensional images;
        overlay a computer model of the component on the three-dimensional point cloud;
        project the computer model on the two-dimensional images;
        select at least two reference points appearing in each image of a subset of images selected from the two-dimensional images;
        determine locations of the at least two reference points in the three-dimensional point cloud;
        determine an image distance between the locations; and
        determine an amount of wear based on the image distance.

2. The wear measurement system of claim 1, wherein the controller is further configured to:
    select at least one feature appearing in each of the two-dimensional images;
    determine positions and orientations of the imaging device for each of the two-dimensional images based on positions of the at least one feature in the two-dimensional images; and
    generate the three-dimensional point cloud based on the positions and orientations of the imaging device and the positions of the at least one feature in the two-dimensional images.

3. The wear measurement system of claim 2, wherein the controller is further configured to:
    select a first set of register points associated with features in the computer model;
    select a second set of register points in the two-dimensional images, the second set of register points corresponding to the features associated with the first set of register points;
    determine register point locations corresponding to the second set in the three-dimensional point cloud; and
    overlay the computer model on the three-dimensional point cloud by orienting the three-dimensional point cloud such that the first set of register points in the computer model overlap with the register point locations in the three-dimensional point cloud.

4. The wear measurement system of claim 3, wherein the at least two reference points include:
    a first reference point positioned on a projection of the computer model on each of the subset of images, and
    a second reference point positioned on the component in each of the subset of images.

5. The wear measurement system of claim 4, wherein the controller is configured to identify the locations of the first reference point and the second reference point by:
    determining positions of the imaging device relative to the component for the subset of images;
    projecting rays from the determined positions of the imaging device through the at least two reference points; and determining the locations of the first reference point and the second reference point in the three-dimensional point cloud based on intersections of the rays.

6. The wear measurement system of claim 5, wherein the controller is further configured to:
determine the image distance between the locations of the first reference point and the second reference point; and
convert the image distance into an actual distance based on a scaling factor.

7. The wear measurement system of claim 6, wherein the scaling factor is based on a dimension determined from the computer model.

8. The wear measurement system of claim 7, wherein the controller is configured to:
select a first image from the subset;
select a second image from the subset;
project a first ray originating at a first position of the imaging device, corresponding to the first image, the first ray passing through the first reference point in the first image;
project a second ray originating at a second position of the imaging device, corresponding to the second image, the second ray passing through the first reference point in the second image; and
determine a location of the first reference point in the three-dimensional point cloud based on an intersection of the first ray and the second ray.

9. The wear measurement system of claim 8, wherein the controller is configured to determine the location in the three-dimensional point cloud at which a distance between the first ray and the second ray is less than a threshold distance.

10. The wear measurement system of claim 2, wherein the controller is configured to automatically select the at least one feature by comparing the two-dimensional images with an image of the at least one feature stored in a memory associated with the controller.

11. The wear measurement system of claim 2, further including an input device configured to receive inputs from an operator, wherein the controller is configured to select the at least one feature based on the inputs received from the operator.

12. A method of measuring wear on a component, comprising:
obtaining, using an imaging device, a plurality of two-dimensional images of the component;
generating, using a controller, a three-dimensional point cloud of the component based on the two-dimensional images;
overlaying a computer model of the component on the three-dimensional point cloud;
projecting the computer model on the two-dimensional images;
selecting at least two reference points appearing in each image of a subset of images selected from the two-dimensional images;
determining locations of the at least two reference points in the three-dimensional point cloud;
determining an image distance between the locations; and
determining an amount of wear based on the image distance.

13. The method of claim 12, wherein generating the three-dimensional point cloud includes:
selecting at least one feature that appears in each of the two-dimensional images;
determining positions and orientations of the imaging device for each of the two-dimensional images based on positions of the at least one feature in the two-dimensional images; and
generating the three-dimensional point cloud based on the positions and orientations of the imaging device and the positions of the at least one feature in the two-dimensional images.

14. The method of claim 13, wherein selecting the at least two reference points includes:
selecting a first reference point positioned on a projection of the computer model on each of the subset of images, and
selecting a second reference point positioned on the component in each of the subset of images.

15. The method of claim 14, wherein determining the locations of the two reference points includes:
selecting a first image from the subset;
selecting a second image from the subset;
projecting a first ray originating at a first position of the imaging device, corresponding to the first image, the first ray passing through the first reference point in the first image;
projecting a second ray originating at a second position of the imaging device, corresponding to the second image, the second ray passing through the first reference point in the second image;
projecting a third ray originating at the first position of the imaging device, the third ray passing through the second reference point in the first image;
projecting a fourth ray originating at the second position of the imaging device, the fourth ray passing through the second reference point in the second image;
determining a first location of the first reference point in the three-dimensional point cloud based on a first intersection of the first ray and the second ray; and
determining a second location of the second reference point in the three-dimensional point cloud based on a second intersection of the third ray and the fourth ray.

16. The method of claim 15, wherein
determining the first location includes determining where a first distance between the first ray and the second ray is less than a threshold distance, and
determining the second location includes determining where a second distance between the third ray and the fourth ray is less than the threshold distance.

17. The method of claim 16, wherein determining the amount of wear further includes:
determining the image distance between the first location and the second location; and
converting the image distance into an actual distance using a scaling factor.

18. The method of claim 17, further including:
selecting a third reference point positioned on the projection of the computer model on each of the subset of images;
selecting a fourth reference point positioned on the projection of the computer model on each of the subset of images;
determining a third location of the third reference point in the three-dimensional point cloud;
determining a fourth location of the fourth reference point in the three-dimensional point cloud;
determining a reference image distance between the third location and the fourth location;

determining a model distance between the third reference point and the fourth reference point from the computer model; and determining the scaling factor as a ratio of the model distance and the reference image distance.

19. The method of claim 12, wherein selecting the at least one feature includes comparing the two-dimensional images with an image of the at least one feature stored in a memory associated with the controller.

20. The method of claim 12, wherein selecting the at least one feature includes selecting, using an input device, the at least one feature in the plurality of two-dimensional images.

* * * * *